US009719915B2

(12) United States Patent
Kshirsagar et al.

(10) Patent No.: US 9,719,915 B2
(45) Date of Patent: Aug. 1, 2017

(54) GAS CAP FOR OPTICAL SENSOR

(71) Applicants: Abhijeet Vikram Kshirsagar, Pune (IN); Chinmaya Rajiv Dandekar, Pune (IN); Sagar Shivajirao Chavan, Sangli (IN)

(72) Inventors: Abhijeet Vikram Kshirsagar, Pune (IN); Chinmaya Rajiv Dandekar, Pune (IN); Sagar Shivajirao Chavan, Sangli (IN)

(73) Assignee: Cooper Technologies Company, Houston, TX (US)

( * ) Notice: Subject to any disclaimer, the term of this patent is extended or adjusted under 35 U.S.C. 154(b) by 3 days.

(21) Appl. No.: 14/821,539

(22) Filed: Aug. 7, 2015

(65) Prior Publication Data
US 2017/0038294 A1 Feb. 9, 2017

(51) Int. Cl.
*G01N 21/17* (2006.01)
(52) U.S. Cl.
CPC . *G01N 21/1702* (2013.01); *G01N 2021/1704* (2013.01); *G01N 2201/067* (2013.01)
(58) Field of Classification Search
USPC ................................................. 73/24.1, 24.02
See application file for complete search history.

(56) References Cited

U.S. PATENT DOCUMENTS

| 4,017,373 A * | 4/1977 | Shaw | G01N 33/0027 |
| | | | 204/432 |
| 5,753,797 A * | 5/1998 | Forster | G01N 21/1702 |
| | | | 250/343 |
| 6,006,585 A * | 12/1999 | Forster | G01N 21/1702 |
| | | | 250/343 |
| 6,939,717 B2 * | 9/2005 | Jiang | E21B 47/011 |
| | | | 436/121 |
| 8,117,897 B2 | 2/2012 | Schropp, Jr. et al. | |
| 2015/0011852 A1 | 1/2015 | Van Kesteren et al. | |

FOREIGN PATENT DOCUMENTS

| WO | 0182792 | 11/2001 |
| WO | 2013151890 | 10/2013 |
| WO | 2014159524 | 10/2014 |

OTHER PUBLICATIONS

V. Renteev, International Search Report and Written Opinion issued in PCT/US2016/045194, completion date Nov. 2, 2016, mailing date Nov. 10, 2016, 6 pages, Federal Institute of Industrial Property, Moscow, Russia.

* cited by examiner

*Primary Examiner* — Paul West
*Assistant Examiner* — Mark A Shabman
(74) *Attorney, Agent, or Firm* — King & Spalding LLP

(57) ABSTRACT

A cap for a gas sensor module is described herein. The cap can include at least one wall forming a cavity having a first portion and a second portion. The cap can also include an inlet tube coupling feature disposed in the at least one wall, where the first location is adjacent to the first portion of the cavity. The cap can further include an outlet tube coupling feature disposed in the at least one wall, where the second location is adjacent to the second portion of the cavity. The cap can also include a distribution channel coupling feature disposed in the at least one wall, where the third location is adjacent to the first portion of the cavity. The cap can further include a receiving channel coupling feature disposed in the at least one wall, where the fourth location is adjacent to the second portion of the cavity.

20 Claims, 5 Drawing Sheets

GAS CAP FOR OPTICAL SENSOR

TECHNICAL FIELD

Embodiments described herein relate generally to gas sensors, and more particularly to systems, methods, and devices for caps for optical gas sensors.

BACKGROUND

The detection and measurement of trace gas concentrations is important for both the understanding and monitoring of a wide variety of applications, such as environmental monitoring, industrial process control analysis, combustion processes, detection of toxic and flammable gases, as well as explosives. For example, trace gas sensors capable of high sensitivity and selectivity can be used in atmospheric science for the detecting and monitoring of different trace gas species including greenhouse gases and ozone, and in breath diagnostics, for detection and monitoring of nitric oxide, ethane, ammonia and numerous other biomarkers. As another example, in gas-to-grid applications, methane generated from a biogas process is tested for impurities (e.g., hydrogen sulfide or $H_2S$) to determine whether the methane is pure enough to be mixed directly with natural gas.

SUMMARY

In general, in one aspect, the disclosure relates to a cap for a gas sensor module. The cap can include at least one wall forming a cavity, where the at least one wall includes at least one sensor head coupling feature, where the at least one sensor head coupling feature is configured to couple to a sensor head of the gas sensor module, and where the cavity has a first portion and a second portion. The cap can also include an inlet tube coupling feature disposed at a first location in the at least one wall, where the first location is adjacent to the first portion of the cavity. The cap can further include an outlet tube coupling feature disposed in a second location in the at least one wall, where the second location is adjacent to the second portion of the cavity. The cap can also include a distribution channel coupling feature disposed at a third location in the at least one wall, where the third location is adjacent to the first portion of the cavity. The cap can further include a receiving channel coupling feature disposed in a fourth location in the at least one wall, where the fourth location is adjacent to the second portion of the cavity.

In another aspect, the disclosure can generally relate to an optical gas sensor. The optical gas sensor can include a sensor head having at least one cap coupling feature, and a cap coupled to the sensor head. The cap of the optical gas sensor can include at least one cap wall forming a cavity, where the at least one cap wall includes at least one sensor head coupling feature, where the at least one sensor head coupling feature couples to the at least one cap coupling feature of the sensor head, and where the cavity has a first portion and a second portion. The cap of the optical gas sensor can also include an inlet tube coupling feature disposed at a first location in the at least one cap wall, where the first location is adjacent to the first portion of the cavity. The cap of the optical gas sensor can further include an outlet tube coupling feature disposed in a second location in the at least one cap wall, where the second location is adjacent to the second portion of the cavity. The cap of the optical gas sensor can also include a distribution channel coupling feature disposed at a third location in the at least one cap wall, where the third location is adjacent to the first portion of the cavity. The cap of the optical gas sensor can further include a receiving channel coupling feature disposed in a fourth location in the at least one cap wall, where the fourth location is adjacent to the second portion of the cavity.

These and other aspects, objects, features, and embodiments will be apparent from the following description and the appended claims.

BRIEF DESCRIPTION OF THE DRAWINGS

The drawings illustrate only example embodiments of caps for optical gas sensors and are therefore not to be considered limiting of its scope, as caps for optical gas sensors may admit to other equally effective embodiments. The elements and features shown in the drawings are not necessarily to scale, emphasis instead being placed upon clearly illustrating the principles of the example embodiments. Additionally, certain dimensions or positionings may be exaggerated to help visually convey such principles. In the drawings, reference numerals designate like or corresponding, but not necessarily identical, elements.

DETAILED DESCRIPTION OF EXAMPLE EMBODIMENTS

Figure 1:
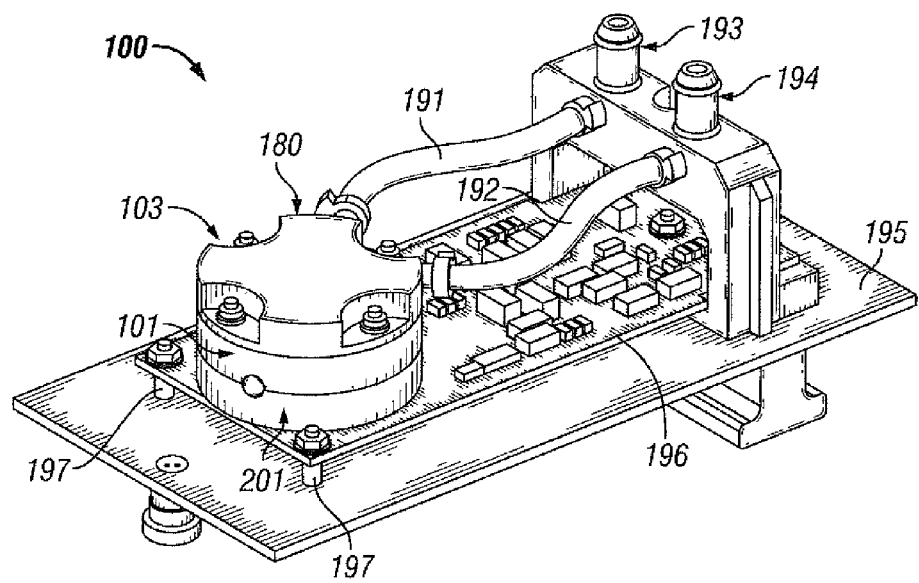
FIG. 1 shows a top-side perspective view of a gas sensor module in accordance with certain example embodiments.

The example embodiments discussed herein are directed to systems, apparatuses, and methods related to caps for optical gas sensors. Optical gas sensors can have a number of configurations and use a number of technologies. For example, a quartz-enhanced photo-acoustic spectroscopic (QEPAS) sensor can have an optical irradiation at a gas-specific wavelength directed through a gap between the prongs of a quartz tuning fork (QTF) vibrating at its resonating frequency. The optical energy is absorbed and released by the gas, causing a change in the resonant frequency of the QTF. The amount of change in the resonant frequency of the QTF is proportional to the concentration of the gas molecules.

While example embodiments are described herein as being directed to optical gas sensors, example embodiments can also be used with other types of sensors. Further, optical gas sensors that can be used with example embodiments can have any of a number of configurations not shown or described herein. As described herein, a user can be any person that interacts with example optical gas sensors. Examples of a user may include, but are not limited to, a consumer, an operations specialist, a gas engineer, a supervisor, a consultant, a contractor, an operator, and a manufacturer's representative.

In one or more example embodiments, example caps for optical gas sensors are subject to meeting certain standards and/or requirements. For example, the International Electrotechnical Commission (IEC) sets standards, such as IEC 60079-28 that applies to optical gas sensors, with which example caps must comply to be used in field applications. Examples of other entities that set applicable standards and regulations include, but are not limited to, the National Electrical Manufacturers Association (NEMA), the National Electric Code (NEC), the Institute of Electrical and Electronics Engineers (IEEE), and Underwriters Laboratories (UL).

In some cases, the example embodiments discussed herein can be used in any type of hazardous environment, including but not limited to an airplane hangar, a drilling rig (as for oil, gas, or water), a production rig (as for oil or gas), a refinery, a chemical plant, a power plant, a mining operation, a wastewater treatment facility, and a steel mill. The caps for optical gas sensors (or components thereof) described herein can be physically placed in and/or used with corrosive components (e.g., gases). In addition, or in the alternative, example caps for optical gas sensors (or components thereof) can be subject to extreme heat, extreme cold, moisture, humidity, dust, and other conditions that can cause wear on the caps for optical gas sensors or portions thereof.

In certain example embodiments, the caps for optical gas sensors, including any components and/or portions thereof, are made of one or more materials that are designed to maintain a long-term useful life and to perform when required without mechanical and/or other types of failure. Examples of such materials can include, but are not limited to, aluminum, stainless steel, fiberglass, glass, plastic, ceramic, and rubber.

Any components (e.g., inlet tube coupling feature, receiving channel) of example caps for optical gas sensors, or portions thereof, described herein can be made from a single piece (as from a mold, injection mold, die cast, or extrusion process). In addition, or in the alternative, a component (or portions thereof) can be made from multiple pieces that are mechanically coupled to each other. In such a case, the multiple pieces can be mechanically coupled to each other using one or more of a number of coupling methods, including but not limited to epoxy, welding, fastening devices, compression fittings, mating threads, and slotted fittings. One or more pieces that are mechanically coupled to each other can be coupled to each other in one or more of a number of ways, including but not limited to fixedly, hingedly, removeably, slidably, and threadably.

Components and/or features described herein can include elements that are described as coupling, fastening, securing, abutting, or other similar terms. Such terms are merely meant to distinguish various elements and/or features within a component or device and are not meant to limit the capability or function of that particular element and/or feature. For example, a feature described as a "coupling feature" can couple, secure, fasten, abut, and/or perform other functions aside from, or in addition to, merely coupling.

A coupling feature (including a complementary coupling feature) as described herein can allow one or more components (e.g., a cap) and/or portions of optical gas sensors to become mechanically and/or electrically coupled, directly or indirectly, to another portion of the optical gas sensor. A coupling feature can include, but is not limited to, a clamp, a portion of a hinge, an aperture, a recessed area, a protrusion, a slot, a spring clip, a tab, a detent, a threaded coupling, and mating threads. One portion of an example optical gas sensor can be coupled to another portion of the optical gas sensor by the direct use of one or more coupling features. In addition, or in the alternative, a portion of an example optical gas sensor can be coupled to another portion of the optical gas sensor using one or more independent devices that interact with one or more coupling features disposed on a component of the optical gas sensor. Examples of such devices can include, but are not limited to, a pin, a hinge, a fastening device (e.g., a bolt, a screw, a rivet), and a spring.

One coupling feature described herein can be the same as, or different than, one or more other coupling features described herein. A complementary coupling feature as described herein can be a coupling feature that mechanically couples, directly or indirectly, with another coupling feature. For any figure shown and described herein, one or more of the components may be omitted, added, repeated, and/or substituted. Accordingly, embodiments shown in a particular figure should not be considered limited to the specific arrangements of components shown in such figure.

Example embodiments of caps for optical gas sensors will be described more fully hereinafter with reference to the accompanying drawings, in which example caps for optical gas sensors are shown. Caps for optical gas sensors may, however, be embodied in many different forms and should not be construed as limited to the example embodiments set forth herein. Rather, these example embodiments are provided so that this disclosure will be thorough and complete, and will fully convey the scope of caps for optical gas sensors to those of ordinary skill in the art. Like, but not necessarily the same, elements (also sometimes called components) in the various figures are denoted by like reference numerals for consistency.

Terms such as "top", "bottom", "left", "right", "inner," "outer," "end," "distal", "proximal", "first", and "second" are used merely to distinguish one component (or part of a component or state of a component) from another. Such terms are not meant to denote a preference or a particular orientation, and are not meant to limit embodiments of caps for optical gas sensors. In the following detailed description of the example embodiments, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Also, the names given to various components described herein are descriptive of example embodiments and are not meant to be limiting in any way. Those skilled in the art will appreciate that a feature and/or component shown and/or described in one embodiment (e.g., in a figure) herein can be used in another embodiment (e.g., in any other figure) herein, even if not expressly shown and/or described in such other embodiment.

FIG. 1 shows a top-side perspective view of a gas sensor module 100 in accordance with certain example embodiments. The gas sensor module 100 of FIG. 1 can include a gas sensor measurement assembly 103, a base 195, a circuit board 196, an inlet header 194, inlet tube 191, an outlet header 193, and outlet tube 192. The gas sensor measurement assembly 103 can include an example cap 180 and a sensor head 202. The sensor head 202 of the gas sensor measurement assembly 103 can include a top portion 101 and a bottom portion 201. The gas sensor measurement assembly 103 is described in more detail below with respect to FIGS. 2A-7

Referring to FIG. 1, the gas sensor measurement assembly 103 can be mounted to any portion of the gas sensor module 100. For example, in this case, the gas sensor measurement assembly 103 is mounted to the circuit board 196. One or more of a number of other components (e.g., integrated circuits, resistors, capacitors) can also be mounted to the circuit board 196. The circuit board 196 can be referred to by any of a number of other names, including a printed circuit board, a PCB, a wiring board, a printed wiring board, and a PWB.

The circuit board 196 can be mounted to the base 195 using one or more of a number of coupling features 197. For example, in this case, each coupling feature 197 can include a standoff positioned between the base 195 and the circuit board 196, a bolt that traverses the standoff, an aperture in the base 195, and an aperture in the circuit board 196, and a nut. One or more other components of the gas sensor module 100 can also be coupled to the base 195. For example, as shown in FIG. 1, an inlet header 194 and an outlet header 193 can be coupled to the base 195.

In such a case, the inlet header 194 can be used to provide the test gas to the gas sensor measurement assembly 103, and the outlet header 193 can be used to received gas that has been tested by the gas sensor measurement assembly 103. The inlet header 194 can send the test gas to the gas sensor measurement assembly 103 through an inlet tube 192 that is coupled therebetween. The inlet header 194 can receive the test gas from any suitable source, whether within or outside of the gas sensor module 100. The inlet tube 192 can be coupled to, or integral with, the inlet header 194. The inlet tube 192 can be made of any of a number of suitable materials.

Similarly, the outlet header 193 can receive the gas that has been tested by the gas sensor measurement assembly 103 through an outlet tube 191 coupled therebetween. The outlet header 193 can deliver the tested gas to any suitable repository, whether within or outside of the gas sensor module 100. The outlet tube 191 can be coupled to, or integral with, the outlet header 193. The outlet tube 191 can be made of any of a number of suitable materials.

Figure 2A:
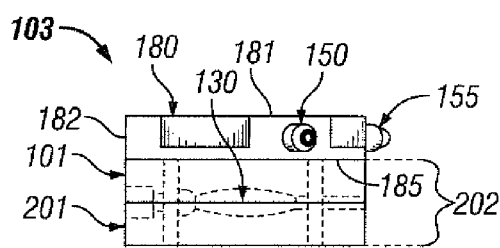
FIGS. 2A and 2B show a gas sensor measurement assembly in accordance with certain example embodiments.
Figure 2B:
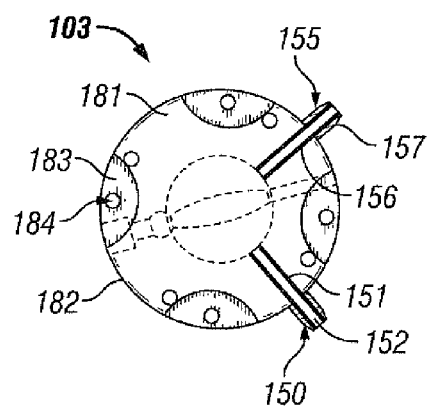
Figure 3A:
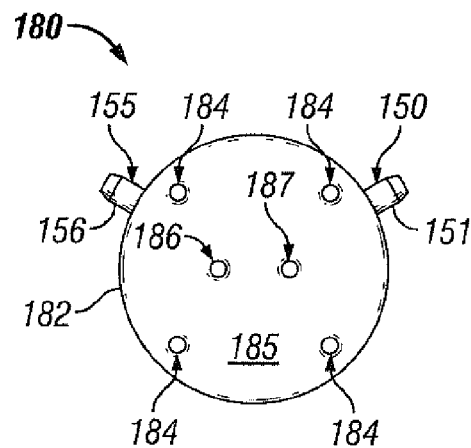
FIGS. 3A-3C show various views of a cap in accordance with certain example embodiments.
Figure 3B:
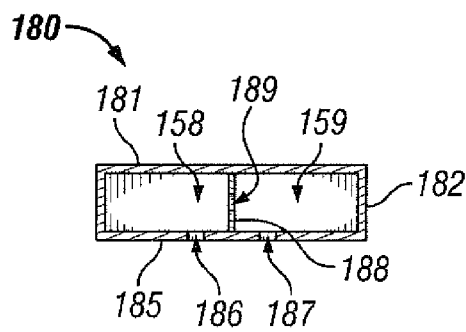
Figure 3C:
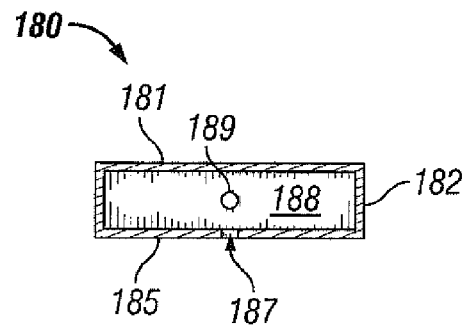

FIGS. 2A and 2B shows a semi-transparent side view and a semi-transparent top view, respectively, of the gas sensor measurement assembly 103 of the gas sensor module 100. FIGS. 3A-3C show various views of the cap 180 of FIGS. 1-2B in accordance with certain example embodiments. Specifically, FIG. 3A shows a bottom view of the cap 180. FIG. 3B shows a cross-sectional side view of the cap 180. FIG. 3C shows another cross-sectional side view of the cap 180, where the view of FIG. 3C is rotated 90° relative to the view of FIG. 3B. The cap 180, including any portions thereof, can be made of one or more materials that are resistant to corrosion and other harmful effects that can be cause by the test gas, the tested gas, and/or the environment in which the gas sensor module 100 is exposed.

Referring to FIGS. 1-3C, the gas sensor measurement assembly 103 is configured to perform any measurements of the gas being tested (also called the test gas herein). For this to occur, the example cap 180 is coupled to the sensor head 202 in such a way that the cap 180 delivers the test gas to the sensor head 202, and also receives the tested gas (the test gas that has been tested) from the sensor head 202. The example cap 180 can include at least one wall that forms a cavity. For example, the cap 180 in this case has a top wall 181, a side wall 182, and a bottom wall 185 that forms the cavity. The cavity can be completely enclosed, substantially enclosed, or partially enclosed. For example, if the bottom wall 185 of the cap 180 of FIGS. 3A-3C is absent, the cavity of the cap 180 would be partially enclosed.

In certain example embodiments, the cavity of the cap 180 has multiple (e.g., two, three, four) portions. For example, in this case the cavity is divided into a first cavity portion 158 and a second cavity portion 159. When the cavity of the cap 180 has multiple cavity portions, each cavity portion can be virtually or physically separated from other cavity portions of the cavity of the cap 180. For example, in this case, the first cavity portion 158 and the second cavity portion 159 are physically separated from each other by a partition 188. In such a case, the partition 188 can have or include one or more of a number of characteristics. Examples of such characteristics can include, but are not limited to, a solid configuration, a porous material, a non-porous material, a mesh, and an orifice (such as orifice 189).

When the portions of the cavity of the cap 180 are physically separated from each other by the partition 188, the partition 188 can substantially isolate one portion (e.g., cavity portion 158) from the other portions (e.g., cavity portion 159). A partition 188 can be temporary or permanent with respect to its position in the cavity of the cap 180. The partition 188 can help separate the test gas from the tested gas. The partition 188 can also help reduce and/or control the flow rate and/or turbulent flow of the test gas, which in turn can control the flow of the test gas sent to the sensor head cavity 130 of the sensor head 202. The partition 188 can also help regulate one or more of a number of parameters (e.g., pressure) within the cavity of the cap 180. If the cavity of the cap 180 has multiple portions, the shape and size of one portion of the cavity can be the same as, or different than, the shape and size of the other portions of the cavity. For example, in this case, cavity portion 158 can have substantially the same shape and size as the cavity portion 159.

In certain example embodiments, the cap 180 is coupled to one or more portions of the sensor head 202. For example, in this case, the cap 180 is coupled to the top portion 101 of the sensor head 202. The cap 180 can be coupled to the sensor head 202 using one or more of a number of coupling features 184 (sometimes called a top portion coupling feature 184). For example, in FIGS. 2A-3C, the coupling features 184 are four apertures that traverse the thickness of the cap 180 and that are disposed substantially equidistantly toward the outer perimeter of the cap 180. In such a case, each coupling feature 184 can receive a fastening device (e.g., a bolt) that is used to couple the cap 180 to the sensor head 202.

The characteristics (e.g., shape, size, configuration) of the coupling features 184 can be configured to correspond to the associated characteristics of coupling features (e.g., coupling features 106 of the top portion 101 of the sensor head 202 (described below with respect to FIG. 4), coupling features 206 of the bottom portion 201 of the sensor head 202 (described below with respect to FIG. 5)) of the sensor head 202. In such a case, the cap 180 can be coupled to the sensor head 202 in one or more certain orientations. The cap 180 can include one or more features to accommodate the coupling features 184. For example, there can be a recessed area 183 (relative to the top wall 181) in which a coupling feature 184 can be disposed. Each coupling feature 184 can be disposed, at least in part, in at least one of the walls (e.g., top wall 181, bottom wall 185) of the cap 180.

In certain example embodiments, the cap 180 receives the test gas from the inlet header 194 through the inlet tube 192. In such a case, the inlet tube 192 is coupled to some portion of the cap 180. For example, as shown in FIGS. 1-2B, the cap 180 can include an inlet tube coupling feature 150 that couples to the inlet tube 192. The inlet tube coupling feature 150 can include one or more of a number of coupling features. For example, in this example, the inlet tube coupling feature 150 can include a tube 151 and a threaded coupling 152 disposed at the distal end of the tube 151. In such a case, the threaded coupling 152 couples to the inlet tube 192.

The proximal end of the tube 151 can be disposed within a wall (e.g., top wall 181, side wall 182, bottom wall 185) of the cap 180 so that the test gas can be delivered to the cavity of the cap 180 or a portion (e.g., cavity portion 158, cavity portion 159) thereof. Put another way, the tube 151 of the inlet tube coupling feature 150 can be disposed in a wall (in this case, the top wall 181) of the cap 180 so that the test gas emitted through the proximal end of the tube 151 is delivered to a portion of the cavity (in this case, cavity portion 159). In such a case, the proximal end of the tube 151 can be disposed along the inner surface of a wall (e.g., the top wall 181) so that the tube 151 is adjacent to that portion of the cavity.

To deliver the test gas from the cap 180 to the sensor head 202, the cap 180 can include a distribution channel coupling feature 187 that can couple to at least one distribution channel (e.g., distribution channel 178 described below with respect to FIGS. 7A and 7B). The distribution channel coupling feature 187 can include one or more of a number of coupling features. For example, in this case, the distribution channel coupling feature 187 is an aperture that is configured to receive and couple to (e.g. abut against) a distribution channel 178. When the distribution channel coupling feature 187 couples to a distribution channel 178, a seamless and continuous channel can be formed therebetween. Alternatively, a sleeve or similar device can be inserted into the distribution channel coupling feature 187 to form, at least in part, a channel between the cap 180 and the gas head 202.

The distribution channel coupling feature 187 can be disposed, at least in part, in a wall (e.g., bottom wall 185) of the cap 180. Further, the distribution channel coupling feature 187 can be located adjacent to a portion (e.g., cavity portion 159) of the cavity. In certain example embodiments, the distribution channel coupling feature 187 is adjacent to the same portion of the cavity as the inlet tube coupling feature 150. For example, in this case, the distribution channel coupling feature 187 and the inlet tube coupling feature 150 are each located adjacent to cavity portion 159 at different positions along a wall (or, in this case, different walls) of the cap 180.

In some cases, the distribution channel coupling feature 187 can be part of the distribution channel 178. The distribution channel 178 transports the test gas from the cap 180 to the sensor head 202. For example, in this case, the distribution channel 178 is disposed in the top portion 101 of the sensor head 202. In certain example embodiments, the distribution channel 178 (or portions thereof) can include a partition, as with the partition 188 described above with respect to the cavity of the cap 180, to help control the flow of the test gas as the test gas flows to the sensor head cavity 130.

To complete the circulation process involving the test gas, once the test gas is tested, the resulting gas (called the tested gas) is removed from the sensor head 202. For example, as shown in FIGS. 1-2B, the cap 180 can include an outlet tube coupling feature 155 that couples to the outlet tube 191. The outlet tube coupling feature 155 can include one or more of a number of coupling features. For example, in this example, the outlet tube coupling feature 155 can include a tube 156 and a threaded coupling 157 disposed at the distal end of the tube 156. In such a case, the threaded coupling 157 couples to the outlet tube 191.

The proximal end of the tube 156 can be disposed within a wall (e.g., top wall 181, side wall 182, bottom wall 185) of the cap 180 so that the test gas can be removed from the cavity of the cap 180 or a portion (e.g., cavity portion 158, cavity portion 159) thereof. Put another way, the tube 156 of the outlet tube coupling feature 155 can be disposed in a wall (in this case, the top wall 181) of the cap 180 so that the tested gas can be received from a portion of the cavity (in this case, cavity portion 158) by the distal end of the tube 156. In such a case, the proximal end of the tube 156 can be disposed along the inner surface of a wall (e.g., the top wall 181) so that the tube 156 is adjacent to that portion of the cavity.

To receive the tested gas by the cap 180 from the sensor head 202, the cap 180 can include a receiving channel coupling feature 186 that can couple to at least one receiving channel (e.g., receiving channel 173 described below with respect to FIGS. 7A and 7B). The receiving channel coupling feature 186 can include one or more of a number of coupling features. For example, in this case, the receiving channel coupling feature 186 is an aperture that is configured to receive and couple to (e.g. abut against) a receiving channel 173. When the receiving channel coupling feature 186 couples to a receiving channel 173, a seamless and continuous channel can be formed therebetween. Alternatively, a sleeve or similar device can be inserted into the receiving channel coupling feature 186 to form, at least in part, a channel between the cap 180 and the gas head 202.

The receiving channel coupling feature 186 can be disposed, at least in part, in a wall (e.g., bottom wall 185) of the cap 180. Further, the receiving channel coupling feature 186 can be located adjacent to a portion (e.g., cavity portion 158) of the cavity. In certain example embodiments, the receiving channel coupling feature 186 is adjacent to the same portion of the cavity as the outlet tube coupling feature 155. For example, in this case, the receiving channel coupling feature 186 and the outlet tube coupling feature 155 are each located adjacent to cavity portion 158 at different positions along a wall (or, in this case, different walls) of the cap 180.

In some cases, the receiving channel coupling feature 186 can be part of the receiving channel 173. The receiving channel 173 transports the tested gas from the sensor head 202 to the cap 180. For example, in this case, the receiving channel 173 is disposed in the top portion 101 of the sensor head 202. In certain example embodiments, the receiving channel 173 (or portions thereof) can include a partition, as with the partition 188 described above with respect to the cavity of the cap 180, to help control the flow of the tested gas as the tested gas flows from the sensor head cavity 130 to the cavity of the cap 180.

In certain example embodiments, a portion of the cavity of the cap 180 can include one or more features that channel the flow of gas (e.g., test gas, tested gas) through that portion of the cavity. Examples of such features can include, but are not limited to, contoured inner surfaces of a wall and baffles. For example, cavity portion 159 can include baffles that channel test gas that flows from the tube 152 of the inlet tube coupling feature 150 through the cavity portion 159 to the distribution channel coupling feature 187.

Figure 4:
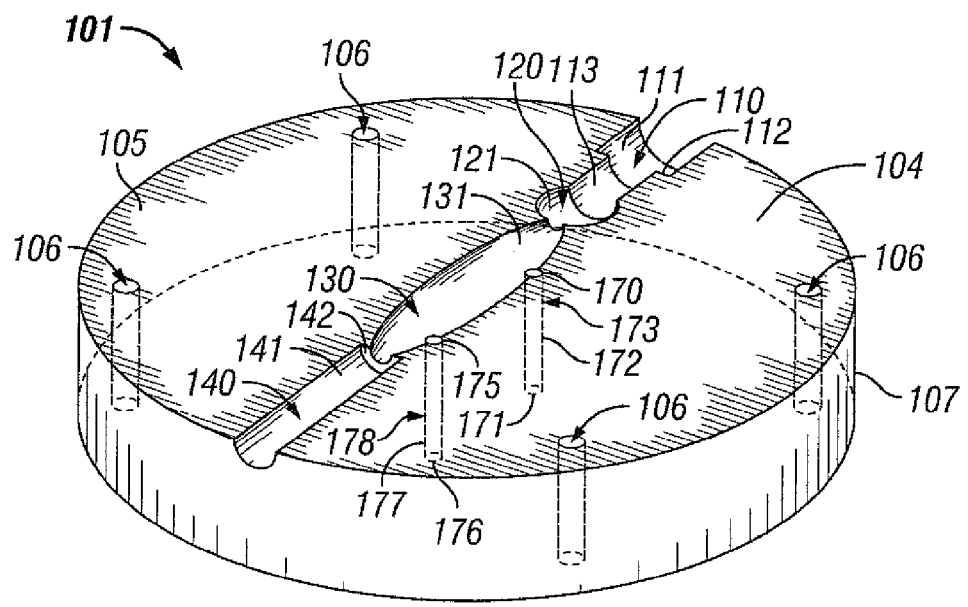
FIG. 4 shows a bottom view of a top portion of a sensor head in accordance with certain example embodiments.

FIG. 4 shows a semi-transparent bottom-side perspective view of the top portion 101 of the sensor head 202 in accordance with certain example embodiments. Referring to FIGS. 1-4, the top portion 101 of the sensor head 201 can have one or more of any of a number of configurations. For example, in this case, the top portion 101 includes a body 104 having an inner surface 105, an outer surface 108 opposite the inner surface 105, and at least one side 107. The top portion 101 of the sensor head 202 can have any of a number of shapes and sizes. For example, the top portion 101 of the sensor head 202 shown in FIG. 4 is cylindrical in shape. The top portion 101 of the sensor head 202 can be made from one or more of a number of suitable materials, including but not limited to stainless steel and nickel-based alloys. The material of the top 101 portion of the sensor head 202 can be resistant to one or more of a number of corrosive materials, including but not limited to hydrogen sulfide ($H_2S$) gas.

In certain example embodiments, a number of cavities are disposed in the body 104 of the top portion 101 along the inner surface 105. For example, a light source cavity 110 (or a portion thereof) can be formed by a light source cavity wall 111, a light source cavity wall 113, and a collar 112 disposed therebetween. The light source cavity 110 can have a shape and size to host one or more of a number of light sources (as shown and described below with respect to FIG. 6). The light source cavity 110 can be disposed at any location along the inner surface 105. For example, as shown in FIG. 4, the light source cavity 110 can be disposed at one end (e.g., close to the side 107) of the top portion 101 of the sensor head 202.

Figure 6:
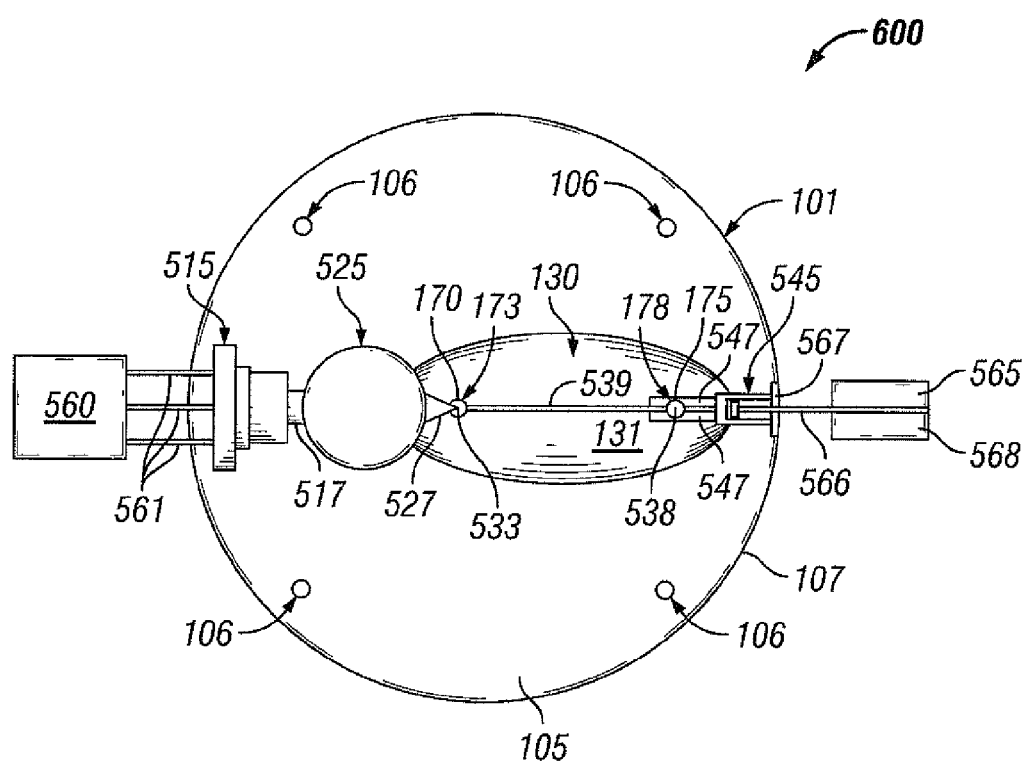
FIG. 6 shows a bottom view of a sensor subassembly in accordance with certain example embodiments.

As another example, an optical device cavity 120 (or a portion thereof) can be formed by an optical device cavity wall 121 and a collar 122. The optical device cavity 120 can have a shape and size to host one or more of a number of optical devices (as shown and described below with respect to FIG. 6). The optical device cavity 120 can be disposed at any location along the inner surface 105. For example, as shown in FIG. 6, the optical device cavity 120 can be disposed adjacent to the light source cavity 110 so that optical device cavity wall 121 is adjacent to the light source cavity wall 113.

As yet another example, an ellipsoidal cavity 130 (or a portion thereof) can be formed by an ellipsoidal cavity wall 131. The ellipsoidal cavity 130 (sometimes called a sensor head cavity 130 or, simply, a cavity 130) can have a shape and size sufficient to receive and reflect light emitted from a light source multiple times and mix the reflected light with gas disposed in the ellipsoidal cavity 130. The ellipsoidal cavity 130 can be disposed at any location along the inner surface 105. For example, as shown in FIG. 6, the ellipsoidal cavity 130 can be disposed adjacent to the optical device cavity 120 so that the ellipsoidal wall 131 is adjacent to the collar 122.

While called an ellipsoidal cavity 130 herein, the shape of the ellipsoidal cavity 130 can be something other than ellipse (e.g., a sphere). Regardless of the shape of the cavity 130, there can be one or more points of reference in the cavity 130 based on the shape. For example, when the cavity 130 is shaped as an ellipse, the ellipse can have a center, two focal points, and two end points. Examples of some of these reference points are described below with respect to FIG. 6.

In certain example embodiments, the top portion 101 of the sensor head 202 can have one or more channels (e.g., channel 173, channel 178) disposed in the body 104. Such channels can be used, for example, to inject test gas into and/or remove tested gas from the ellipsoidal cavity 130. Channel 178 can be disposed in a different location (relative to the location of channel 173) in the body 104 of the top portion 101 of the sensor head 202. Each channel can have any of a number of features, shapes, sizes, and/or orientations. For example, in this case, channel 173 can include a channel wall 172 disposed in the body 104 of the top portion 101 and that is substantially linear. The channel 173 in this case also has a first end 171 disposed at the outer surface 108 and a second end 170 disposed at the ellipsoidal cavity wall 131 (adjacent to the ellipsoidal cavity 130). The first end 171 can be coupled to a coupling feature (e.g., receiving channel coupling feature 186) of the example cap 180.

Similarly, channel 178 can include a channel wall 177 disposed in the body 104 of the top portion 101 and that is substantially linear. The channel 178 in this case also has a first end 176 disposed at the outer surface 108 and a second end 175 disposed at the ellipsoidal cavity wall 131 (adjacent to the ellipsoidal cavity 130). The first end 176 can be coupled to a coupling feature (e.g., distribution channel coupling feature 187) of the example cap 180. In this case, channel 173 is substantially parallel with channel 178. The channel wall of a channel can be coated with one or more of a number of materials. In addition, or in the alternative, the channel wall of a channel can have a sleeve or some similar component of the gas sensor module disposed therein. In certain example embodiments, a channel is aligned with a reference point of the ellipsoidal cavity 130. For example, channel 173 can be aligned with one focal point of the ellipsoidal cavity 130, and channel 178 can be aligned with the other focal point of the ellipsoidal cavity 130.

The first end (e.g., first end 171, first end 176) of a channel can also be at the side 107, the inner surface 105, or at some other location on the top portion 101, depending on one or more of a number of factors, including but not limited to the characteristics (e.g., shape, size, orientation) of the cap 180 disposed adjacent to the top portion 101 of the sensor head 202, and the location of one or more components (e.g., a gas injector, a gas collector) of the gas sensor module. A channel (e.g., channel 173, channel 178) can be linear, curved, angled, and/or have one or more of any other shapes. Similarly, a channel wall (e.g., channel wall 172, channel wall 177) of a channel can have any of a number of characteristics (e.g., size, cross-sectional shape, length, width) suitable for the gas sensor module.

As still another example, a tuning fork cavity 140 (or portion thereof) can be formed by a tuning fork cavity wall 141 and a collar 142. The tuning fork cavity 140 can have a shape and size to host one or more of a number of tuning forks (as shown and described below with respect to FIG. 6). The tuning fork cavity 140 can be disposed at any location along the inner surface 105. For example, as shown in FIG. 6, the tuning fork cavity 140 can be disposed adjacent to the ellipsoidal cavity 130 so that the collar 142 is adjacent to the ellipsoidal cavity wall 131. In addition, the tuning fork cavity 140 can be disposed at another end (e.g., close to the side 107) of the portion of the top portion 101 of the sensor head 202. In such a case, the tuning fork cavity 140 can be located at an opposite end of the top portion 101 of the sensor head 202 relative to the light source cavity 110.

In certain example embodiments, the light source cavity 110, the optical device cavity 120, the ellipsoidal cavity 130, and the tuning fork cavity 140 can be aligned substantially linearly with each other and have a common axis that runs along the length of each cavity. In certain example embodiments, there are multiple portions of the sensor head 202. For example, as described above, there may be two symmetrical pieces of the sensor head 202, where one piece is the top portion 101 of the sensor head 202 shown in FIG. 6, and the other piece is the bottom portion 201 shown in FIG. 4 below. In such a case, when the two pieces are joined together, the various cavities become enclosed and walls that define those cavities become substantially continuous.

In certain example embodiments, the top portion 101 of the sensor head 202 includes one or more of a number of coupling features 106 that allow the top portion 101 of the sensor head 202 to become coupled, directly or indirectly, to another component (e.g., bottom portion 201, cap 180) of the gas sensor module 100. For example, in this case, there are four coupling features 106 that are spaced substantially equidistantly from each other toward the outer perimeter of the inner surface 105 of the top portion 101. Each coupling feature 106 can have any of a number of features and/or configurations. For example, in this case, each coupling feature 106 is an aperture that traverses the thickness of the body 104 of the top portion 101.

The coupling features 106 (sometimes called a cap coupling feature 106 and/or a bottom portion coupling feature 206) of the top portion 101 can have the same size and orientation compared to the shape and size of the coupling features 184 of the cap 180 and the coupling features 206 of the bottom portion 201 (as described below). In this way, when the top portion 101 abuts against the cap 180 (along the top of the top portion 101) and the bottom portion 201 (along the bottom of the top portion 101), the coupling features 184, the coupling features 106, and the coupling features 206 are all aligned with each other so that one or more fastening devices can be disposed therein to couple the cap 180, the top portion 101, and the bottom portion 201 together.

Figure 5:
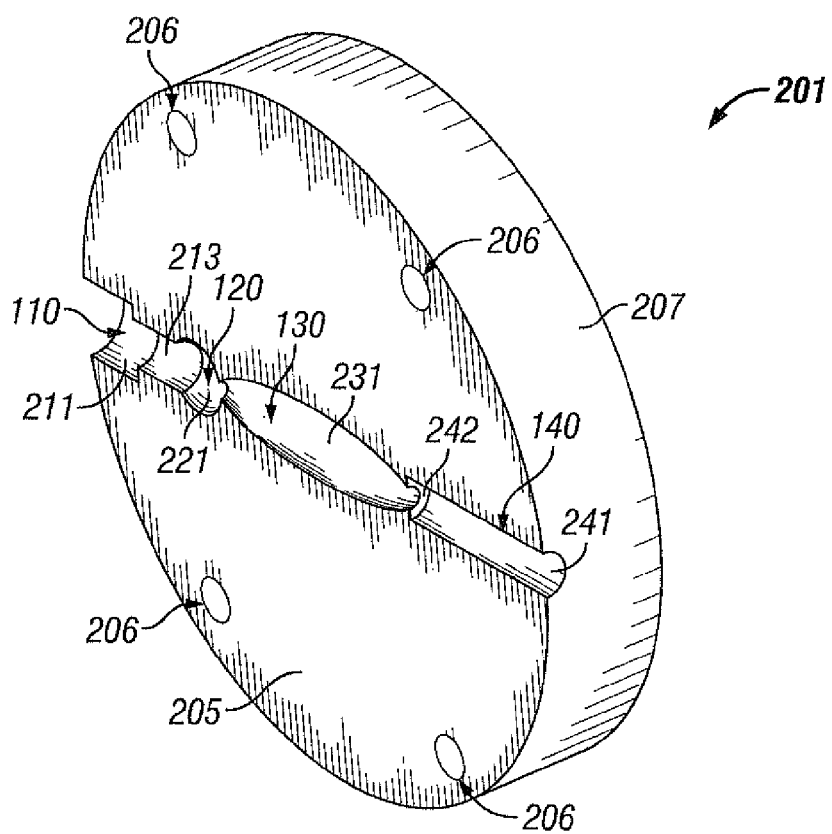
FIG. 5 shows a top perspective view of a bottom portion of a sensor head in accordance with certain example embodiments.

FIG. 5 shows a side-top perspective view of the bottom portion 202 of the sensor head 202 in accordance with certain example embodiments. Referring to FIGS. 1-4, the bottom portion 201 of a sensor head 202 of FIG. 5 is substantially the same as the top portion 101 of a sensor head 202 of FIG. 4, except as described below. In other words, the bottom portion 201 of a sensor head 202 is substantially the mirror image of the top portion 101 of the sensor head 202. In this case, unless stated otherwise below, a component (e.g., inner surface 105, ellipsoidal wall 131) of the top portion 101 has a corresponding component (e.g., inner surface 205, ellipsoidal wall 231) of the bottom portion 201, where the last two digits of such component of the top portion 101 and the corresponding component of the bottom portion 201 are the same.

In this case, the bottom portion 201 of FIG. 5 does not include any channels, such as channel 173 and channel 178 of the top portion 101 of FIG. 4. Also, the coupling features 206 (sometimes called a top portion coupling feature 206) of the bottom portion 201 may only traverse some, instead of all, of the thickness of the body 204 of the bottom portion 201. Again, when the inner surface 105 of the top portion 101 and the inner surface 205 of the bottom portion 201 abut against each other, and when the coupling features 106 of the top portion 101 are coupled (directly or indirectly) to the coupling features 206 of the bottom portion 201, the various cavities of the sensor head 202 become substantially whole and continuous.

FIG. 6 shows a bottom view of a sensor subassembly 600 in accordance with certain example embodiments. Specifically, the sensor subassembly 600 of FIG. 6 includes the top portion 102 of the sensor head 202, a light source 515, a power source 560, an optical device 525, a tuning fork 545, a driver 565, and a receiver 568. Referring to FIGS. 1-6, the light source 515 is disposed in the light source cavity 110 (hidden from view), the optical device 525 is disposed in the optical device cavity 120 (hidden from view), and the tuning fork 545 is disposed in the tuning fork cavity 140 (hidden from view) of the top portion 101 of the sensor head 202.

The light source 515 can use any type of lighting technology (e.g., light emitting diode, a laser diode (also called a semiconductor laser)) that generates light 517 that is directed toward the optical device 525. The light source 515 can have a shape and size that conforms to one or more contours of the light source cavity 510. The light 517 generated and emitted by the light source 515 can be of any suitable wavelength, depending on one or more of a number of factors, including but not limited to the gas being tested, the temperature, and the characteristics of the optical device 525. The light source 515 can be coupled to the power source 560 (e.g., a driver), which can provide power and/or control signals to the light source 515. The light source 515 can include one or more of a number of components, including but not limited to a light element (e.g., a diode, a bulb) and a circuit board.

In certain example embodiments, the optical device 525 is any type of device capable of receiving light 517 from the light source 515 and processing the light 517 to create light 527 that is transmitted to a particular location within the ellipsoidal cavity 130. The optical device 525 can have an outer surface 526 that abuts against some or all of the wall 121 and the collar 122 that forms the optical device cavity 120 in the top portion 101 (as well as in the corresponding parts of the bottom portion 201) of the sensor head 202. The optical device 525 can have any shape (e.g., sphere, semisphere, pyramid) and size that conforms to one or more contours of the optical device cavity 120.

The optical device 525 can be made of one or more suitable materials, including but not limited to silica and glass. In any case, the optical device 525 is resistant to corrosive materials, such as $H_2S$ gas. In order for the optical device 525 to transmit the light 527 to a particular location (in this case, focal point 533) within the ellipsoidal cavity 130, a number of factors must be balanced. Such factors can include, but are not limited to, the orientation of the optical device 525, the material of the optical device 525, the position of the optical device 525 relative to the ellipsoidal cavity 130 and the light source 515, and the wavelength of the light 517. In certain example embodiments, a sealing member (e.g., a gasket, an o-ring, silicone) can be used to provide a barrier that prevents potentially corrosive materials in the ellipsoidal cavity 130 from entering the optical device cavity 120 or the light source cavity 110.

The ellipsoidal cavity 130 has one or more walls 131 that are optically and acoustically reflective. If the ellipsoidal cavity 130 is formed by more than one piece, as shown in these figures, then the walls of the pieces (e.g., ellipsoidal wall 131 of the top portion 101, ellipsoidal wall 231 of the bottom portion 201) are highly machined so that the junctions where the multiple pieces meet within the ellipsoidal cavity 130 provide little to no substantial degradation of the optical and acoustic reflective uniformity relative to the rest of the walls of the ellipsoidal cavity 130. In certain example embodiments, the ellipsoidal cavity 130 has two focus points (in this case, focus point 533 and focus point 538) that are positioned along the major axis 539 of the ellipsoidal cavity 130. In some cases, as shown in FIG. 5, the major axis 539 of the ellipsoidal cavity 130 can extend along the substantial center (longitudinal axis) of the optical cavity 120, the light source cavity 110, and/or the tuning fork cavity 140.

In certain example embodiments, the light 527 transmitted from the optical device 525 is directed to focus point 533 within the ellipsoidal cavity 130. In such a case, the light (optical waves) passes through the focus point 533 and is reflected off of one or more walls (e.g., wall 131, wall 231)

at least one time to converge at focus point 538 within the ellipsoidal cavity 130. Also disposed within the ellipsoidal cavity 130 in certain example embodiments is a gas.

The test gas in the ellipsoidal cavity 130 can include one or more elements (e.g., carbon, hydrogen) that can combine to form one or more compounds (e.g., methane). In some cases, the gas can also have impurities (e.g., $H_2S$) that can be detected, both in existence and in amount, using the optical gas sensor. As discussed above, the gas can be injected into the ellipsoidal cavity 130 through one or more channels (e.g., channel 178) disposed in the body 104 of the top portion 101 of the sensor head 202, entering the ellipsoidal cavity 130 through the second end 175 (also called a gas entry port 175) of the channel 178.

The positioning of the gas entry port 175 and/or the alignment of the channel wall 177 of the channel 178 can coincide with a reference point of the ellipsoidal cavity 130. For example, in this case, the channel 178 is configured to direct the gas toward the focus point 533. Alternatively, the channel 178 can be configured to direct the gas at some other point or area of the ellipsoidal cavity 130. For example, the gas entry port 175 can be disposed at any point on the wall 131 so that the gas is directed between focus point 533 and focus point 538 of the ellipsoidal cavity 130.

When the gas molecules interact with the light waves (derived from light 527) reflected off the wall (e.g., wall 131) in the ellipsoidal cavity 130, the gas molecules become stimulated. Thus, the channel 178 is positioned and/or configured in such a way that the gas emitted through the gas entry port 175 can more easily interact with the reflected light waves within the ellipsoidal cavity 130.

As discussed below, the tines 547 of a tuning fork 545, disposed in the tuning fork cavity 140, can be positioned such that the focus point 538 is disposed between the tines 547. The energy released by the gas molecules, stimulated by the light waves 539 in the ellipsoidal cavity 130, reach the focus point 538 and interact with the tines 547 of the tuning fork 545. In such a case, the stimulated gas molecules change the frequency at which the tines 547 vibrate. The parameters of the light source 515 and/or the optical device 525 (or portions thereof, such as the laser) are selected so that only a particular gas can cause such interactions with the tines 547 of the tuning fork 545. In certain example embodiments, the light 539 emitted by the optical 525 device is directed between (in some cases, at a particular point between) the tines 547 of the tuning fork 545.

As discussed above, the tuning fork 545 (or portions thereof) can be made of quartz. The tuning fork 545 can be any type of device that vibrates at one or more frequencies. The tuning fork 545 can have one or more components. For example, in this case, the tuning fork 545 has multiple (e.g., two) tines 547 and a base 546 from which the tines 547 extend. The tines 547 can be at least partially flexible, so that the shape of the tines 547 can change. When the shape of the tines 547 changes, the tines 547 can vibrate at a different frequency. The tuning fork 545 (including any of its components, such as the tines 547) can be made of any suitable material, including but not limited to quartz. In any case, the tuning fork 545 can be resistant to corrosive materials, such as $H_2S$ gas.

The tines 547 of the tuning fork 545 can be oriented in any of a number of suitable ways within the ellipsoidal cavity 130. For example, the tines 547 can be substantially parallel to major axis 539 of the ellipsoidal cavity 130, which includes the focus point 533 and the focus point 538. In certain example embodiments, a sealing member (e.g., a gasket, an o-ring, silicone) (not shown) can be used to provide a barrier that prevents potentially corrosive materials in the ellipsoidal cavity 130 from entering the tuning fork cavity 140. In certain example embodiments, the tines 547 of the tuning fork 545 are made of or coated with a material that is resistant to corrosive elements, such as $H_2S$.

The tines 547 of the tuning fork 545 can vibrate based on something other than the stimulated gas molecules within the ellipsoidal cavity 130. For example, a driver 565 can be coupled to the tuning fork 545. In such a case, the driver 565 can provide a vibration frequency to the tuning fork 545, causing the tines 547 to vibrate at a certain frequency. Such a frequency may be substantially similar to a frequency induced by a pure form (without any impurities) of the gas being stimulated within the ellipsoidal cavity 130.

To measure the frequency at which the tines 547 of the tuning fork 545 are vibrating, one or more measuring devices can be used. For example, as shown in FIG. 6, a receiver 568 can be coupled to the tuning fork 545. In such a case, the receiver 568 can determine a vibration frequency to the tuning fork 545. Thus, when the vibration frequency of the tines 547 changes, the measured change can be directly correlated to an impurity in the gas injected through the channel into the ellipsoidal cavity 130.

The driver 565 and/or the receiver 568 can be coupled to the tuning fork 545 in one or more of a number of ways. For example, as shown in FIG. 6, an adapter 567 can be mechanically coupled to the base 546 of the tuning fork 545, and one or more electric conductors 566 can be coupled between the adapter 567 and the driver 565 and/or the receiver 568. In certain alternative embodiments, wireless technology can be used to couple the driver 565 and/or the receiver 568 to the tuning fork 545.

Figure 7A:
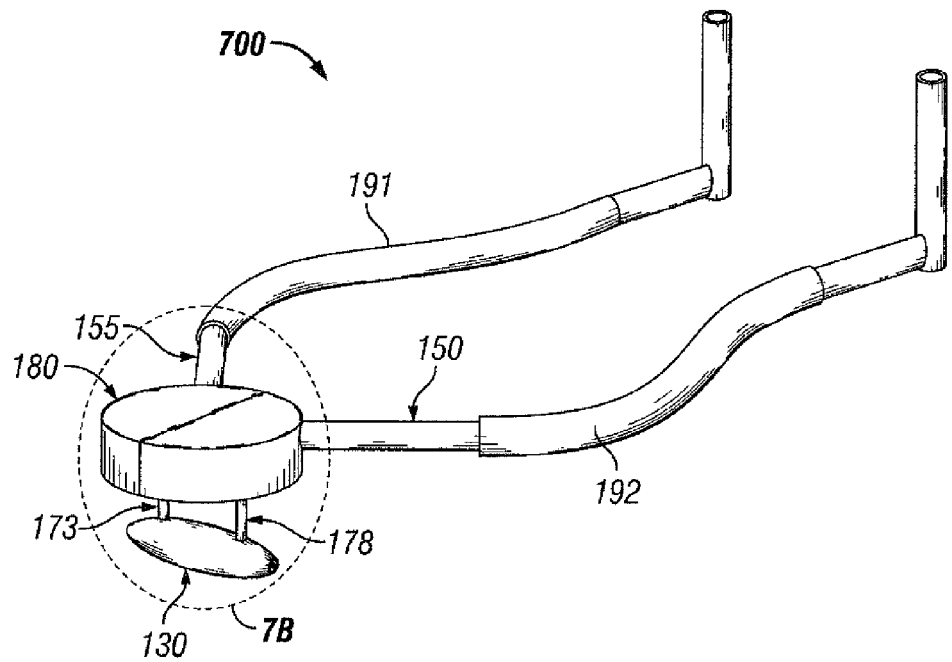
FIGS. 7A and 7B show another sensor subassembly in accordance with certain example embodiments.
Figure 7B:
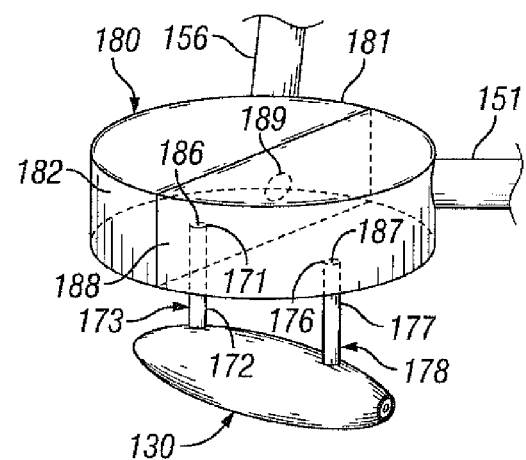

FIGS. 7A and 7B show another sensor subassembly 700 in accordance with certain example embodiments. Referring to FIGS. 1-7B, the sensor subassembly 700 of FIGS. 7A and 7B shows the cap 180, the inlet tube 192 coupled to the inlet tube coupling feature 150 of the cap 180, the outlet tube 192 coupled to the outlet tube coupling feature 155 of the cap 180, the distribution channel 178, the receiving channel 173, and the sensor head cavity 130 (without the sensor head). In FIG. 7B, the cap 180 is shown as semi-transparent to show the partition 188 and the orifice 189 in the partition 188.

Example embodiments provide a number of benefits. Examples of such benefits include, but are not limited to, compliance with one or more applicable standards (e.g., IP65, IEC 60079-28, Zone 1 or Zone 2 compliance), ease in maintaining and replacing components, and more accurate and quicker detection and measurement of impurities in gases. The example cap described herein can reduce/control the effects of flow and/or turbulence of the test gas and/or the tested gas. Example embodiments can also allow for better alignment accuracy within the sensor head cavity so that the test gas can be more accurately tested. The shape, size, and other characteristics of the various components of a gas sensor module, including the example cap described herein, can be engineered to achieve optimal flow rate, minimal turbulence, optimal efficiency, and/or any of a number of other performance metric.

Although embodiments described herein are made with reference to example embodiments, it should be appreciated by those skilled in the art that various modifications are well within the scope and spirit of this disclosure. Those skilled in the art will appreciate that the example embodiments described herein are not limited to any specifically discussed application and that the embodiments described herein are illustrative and not restrictive. From the description of the example embodiments, equivalents of the elements shown therein will suggest themselves to those skilled in the art, and ways of constructing other embodiments using the present disclosure will suggest themselves to practitioners of the art. Therefore, the scope of the example embodiments is not limited herein.

What is claimed is:

1. A cap for a gas sensor module, the cap comprising:
   at least one wall forming a cavity, wherein the at least one wall comprises at least one sensor head coupling feature, wherein the at least one sensor head coupling feature is configured to couple to a sensor head of the gas sensor module, and wherein the cavity comprises a first portion and a second portion;
   an inlet tube coupling feature disposed at a first location in the at least one wall, wherein the first location is adjacent to the first portion of the cavity, wherein the inlet tube coupling feature is configured to couple to an inlet tube through which a test gas flows into the first portion of the cavity;
   an outlet tube coupling feature disposed in a second location in the at least one wall, wherein the second location is adjacent to the second portion of the cavity, wherein the outlet tube coupling feature is configured to couple to an outlet tube through which a tested gas flows from the second portion of the cavity;
   a distribution channel coupling feature disposed at a third location in the at least one wall, wherein the third location is adjacent to the first portion of the cavity, wherein the distribution channel coupling feature is configured to send the test gas to the sensor head;
   a receiving channel coupling feature disposed in a fourth location in the at least one wall, wherein the fourth location is adjacent to the second portion of the cavity, wherein the receiving channel coupling feature is configured to receive the tested gas from the sensor head; and
   a partition disposed within the cavity, wherein the partition divides the cavity into the first portion and the second portion, and wherein the partition is configured to reduce a flow rate of the test gas through the distribution channel to the sensor head.

2. The cap of claim 1, wherein the distribution channel coupling feature comprises a first aperture and is configured to couple to a distribution channel, and wherein the receiving channel coupling feature comprises a second aperture and is configured to couple to a receiving channel.

3. The cap of claim 2, wherein the first portion of the cavity comprises at least one baffle to channel a flow of gas from the inlet tube coupling feature to the distribution channel coupling feature.

4. The cap of claim 1, wherein the partition substantially isolates the first portion of the cavity from the second portion of the cavity.

5. The cap of claim 1, wherein the partition comprises at least one orifice that traverses therethrough.

6. The cap of claim 5, wherein the at least one orifice comprises a mesh configuration.

7. The cap of claim 1, wherein the at least one sensor head coupling feature comprises an aperture that traverses the at least one wall, wherein the aperture is configured to receive a fastening device used to couple the at least one wall to the sensor head.

8. The cap of claim 1, wherein the inlet tube coupling feature is configured to couple to an inlet tube of the gas sensor module, and wherein the outlet tube coupling feature is configured to couple to an outlet tube of the gas sensor module.

9. The cap of claim 1, wherein the gas sensor module is an optical gas sensor module.

10. The cap of claim 1, wherein the at least one wall is resistant to corrosion.

11. The cap of claim 1, wherein the at least one wall comprises a top wall, a bottom wall, and a side wall that substantially enclose the cavity.

12. The cap of claim 1, wherein the partition further controls turbulence of the test gas through the distribution channel to the sensor head comprises.

13. An optical gas sensor, comprising:
    a sensor head comprising at least one cap coupling feature; and
    a cap coupled to the sensor head, wherein the cap comprises:
    at least one cap wall forming a cavity, wherein the at least one cap wall comprises at least one sensor head coupling feature, wherein the at least one sensor head coupling feature couples to the at least one cap coupling feature of the sensor head, and wherein the cavity comprises a first portion and a second portion;
    an inlet tube coupling feature disposed at a first location in the at least one cap wall, wherein the first location is adjacent to the first portion of the cavity, wherein the inlet tube coupling feature is configured to couple to an inlet tube through which a test gas flows into the first portion of the cavity;
    an outlet tube coupling feature disposed in a second location in the at least one cap wall, wherein the second location is adjacent to the second portion of the cavity, wherein the outlet tube coupling feature is configured to couple to an outlet tube through which a tested gas flows from the second portion of the cavity;
    a distribution channel coupling feature disposed at a third location in the at least one cap wall, wherein the third location is adjacent to the first portion of the cavity, wherein the distribution channel coupling feature sends the test gas to the sensor head;
    a receiving channel coupling feature disposed in a fourth location in the at least one cap wall, wherein the fourth location is adjacent to the second portion of the cavity, wherein the receiving channel coupling feature receives the tested gas from the sensor head; and
    a partition disposed within the cavity, wherein the partition divides the cavity into the first portion and the second portion, and wherein the partition reduces a flow rate of the test gas through the distribution channel to the sensor head.

14. The optical gas sensor of claim 13, further comprising:
    an inlet tube coupled to the inlet coupling feature, wherein the inlet tube is further coupled to an inlet header; and
    an outlet tube coupled to the outlet tube coupling feature, wherein the outlet tube is further coupled to an outlet header.

15. The optical gas sensor of claim 13, wherein the sensor head further comprises a sensor head cavity formed by at least one sensor head wall.

16. The optical gas sensor of claim 15, further comprising:
    a distribution channel coupled to the distribution channel coupling feature, wherein the distribution channel is also disposed in the at least one sensor head wall adjacent to the cavity.

17. The optical gas sensor of claim 16, further comprising:
    a receiving channel coupled to the receiving channel coupling feature, wherein the receiving channel is also disposed in the at least one sensor head wall adjacent to the cavity.

18. The optical gas sensor of claim 17, wherein the sensor head cavity has an ellipsoidal shape with a first focus point and a second focus point, wherein the distribution channel is directed toward the first focus point, and wherein the receiving channel is direct toward the second focus point.

19. The optical gas sensor of claim 13, wherein the at least one cap wall, the at least one sensor wall, the distribution channel, and the receiving channel are resistant to corrosion.

20. The optical gas sensor of claim 13, wherein the cap further comprises a partition disposed within the cavity, wherein the partition divides the cavity into the first portion and the second portion.

* * * * *